United States Patent
Suppiger et al.

(10) Patent No.: US 10,918,592 B2
(45) Date of Patent: Feb. 16, 2021

(54) INJECTABLE AQUEOUS IMPLANT FORMULATION CONTAINING ASCORBIC ACID

(71) Applicant: GEISTLICH PHARMA AG, Wolhusen (CH)

(72) Inventors: Daniel Suppiger, Rotkreuz (CH); Paul Buxton, Lucerne (CH); Nino Kurz, Langnau im Emmental (CH)

(73) Assignee: Geistlich Pharma AG, Wolhusen (CH)

( * ) Notice: Subject to any disclaimer, the term of this patent is extended or adjusted under 35 U.S.C. 154(b) by 0 days.

(21) Appl. No.: 16/899,997

(22) Filed: Jun. 12, 2020

(65) Prior Publication Data

US 2020/0390690 A1    Dec. 17, 2020

(30) Foreign Application Priority Data

Jun. 14, 2019 (EP) ..................................... 19180283

(51) Int. Cl.
| | |
|---|---|
| *A61K 9/00* | (2006.01) |
| *A61K 33/06* | (2006.01) |
| *A61M 5/20* | (2006.01) |
| *A61K 31/375* | (2006.01) |
| *A61K 47/42* | (2017.01) |

(52) U.S. Cl.
CPC .......... *A61K 9/0024* (2013.01); *A61K 31/375* (2013.01); *A61K 33/06* (2013.01); *A61K 47/42* (2013.01); *A61M 5/2066* (2013.01)

(58) Field of Classification Search
CPC .... A61K 9/0024; A61K 33/06; A61K 31/376; A61K 47/42; A61M 5/2066
See application file for complete search history.

(56) References Cited

U.S. PATENT DOCUMENTS

| | | |
|---|---|---|
| 4,246,457 A | 1/1981 | Teichert |
| 5,167,961 A | 12/1992 | Heinz |
| (Continued) | | |

FOREIGN PATENT DOCUMENTS

| | | |
|---|---|---|
| EP | 0270254 A2 | 6/1988 |
| EP | 2654816 B1 | 2/2015 |
| (Continued) | | |

OTHER PUBLICATIONS

Alexander et al (Pharmacological Ascorbate Reduces Radiation-Induced Normal Tissue Toxicity and Enhances Tumor Radiosensitization in Pancreatic Cancer, Cancer Res, Dec. 15; 78(24): 6838-6851. (Year: 2018).*

(Continued)

*Primary Examiner* — Carlos A Azpuru
(74) *Attorney, Agent, or Firm* — Rothwell, Figg, Ernst & Manbeck, P.C.

(57) ABSTRACT

An injectable aqueous implant formulation, and processes for making and using the formulation, wherein the injectable aqueous implant formulation has been sterilized by gamma-ray or X-ray-irradiation and can be extruded through a tapering system and an 18 gauge (0.838 mm inner diameter) 25.4 mm long cannula with a force not exceeding 60 N, which comprises 25-45 w/w % of a mixture of nanocrystalline hydroxyapatite particles derived from natural bone having a size of 50 to 200 μm as determined by sieving and fragments of naturally crosslinked fibrous collagen material that pass through a 0.5 mm sieve, whereby the w/w ratio of nanocrystalline hydroxyapatite to collagen is from 1.8 to 4.5, which contains at least 0.05% (w/w) ascorbic acid.

19 Claims, 5 Drawing Sheets

Medmix syringe mixing system (56) References Cited

U.S. PATENT DOCUMENTS

| | | | |
|---|---|---|---|
| 5,352,715 | A | 10/1994 | Wallace et al. |
| 7,322,825 | B2 | 1/2008 | Szymaitis |
| 2003/0026770 | A1 | 2/2003 | Szymaitis |
| 2007/0026030 | A1 | 2/2007 | Gill et al. |
| 2011/0091353 | A1* | 4/2011 | Burgess ............... A61L 2/0035 422/22 |
| 2012/0107401 | A1 | 5/2012 | McKay |
| 2016/0106674 | A1 | 4/2016 | Scalesciani |

FOREIGN PATENT DOCUMENTS

| | | | |
|---|---|---|---|
| EP | 3323437 | A1 | 5/2018 |
| WO | 2019/115792 | * | 6/2019 |
| WO | 2019115792 | A1 | 6/2019 |

OTHER PUBLICATIONS

Geistlich Bio-Oss et al: "Proven Clinical Efficiency Key to Success of Nascent European Bone Graft Substitutes Market", PR Newswire, Sep. 6, 2004 (Sep. 6, 2004), XP55566242, Retrieved from the Internet: URL:https://www.geistlich-na.com/fileadmin/contenVGeistlich_USA/Documents/PDFs/Product_Brochures/GPNA-BoneSubstituteBrochure_2018.pdf.

Cardaropoli, D. et al: "Bio-Oss collagen and orthodontic movement for the treatment of infrabony defects in the esthetic zone", The International journal of periodontics & restorative dentistry, Dec. 1, 2006 (Dec. 1, 2006), p. 553, XP55566245, United States Retrieved from the Internet: URL:http://coimplante.odo.br/Biblioteca/J%20Peridontics%20Restorative%20DenVprd_26_6_Cardaropoli_4.pdf.

Shirmohammadi, A. et al., "Comparative Study on the Efficacy of Anorganic Bovine Bone (Bio-Oss) and Nanocrystalline Hydroxyapatite (Ostim) in Maxillary Sinus Floor Augmentation", International Scholarly Research Notices, vol. 2014, Jan. 1, 2014 (Jan. 1, 2014), pp. 1-7, XP55566246, DOI: 10.1155/2014/967091.

Sheikh et al., "Natural graft tissues and synthetic biomaterials for periodontal and alveolar bone reconstructive applications: a review," Biomaterials Research, published Jun. 5, 2017, p. 1-20.

European Search Report cited in EP 19 18 0283, dated Jan. 24, 2020, 7 pages.

* cited by examiner

Fig. 1:

Medmix syringe mixing system

Fig. 2

Bone-Cement Delivery System
Operating Instruction (using plunger)

MEDMIX

Step 1:
Identification of the system parts:
a) Syringe
b) Syringe cap
c) Luer-cap
d) Mixing device
e) Plunger

Step 2:
Remove the luer-cap from the syringe cap. Attach the container with liquid by turning the container clockwise onto the syringe cap.

Step 3:
Aspirate the liquid from the container by pulling the plunger. Repeat if necessary.

Step 4:
Remove the container by turning counter clock-wise while fixing the syringe cap with two fingers. Close syringe by attaching the luer-cap to the syringe cap.

Step 5:
Remove the plunger sleeve from the mixing device by pushing the handle with the thumb and two fingers.

Step 6:
Mix the biomaterial by moving the mixing device back and forth while simultaneously rotating. Be sure to mix the material at both very ends of the syringe.

Step 7:
Pull back the mixing device completely. Attach the plunger sleeve onto the mixing device by positionning the front end to the piston first.

Step 8:
Remove the luer-cap from the syringe cap. To vent air slowly push the plunger until all air is removed.

Step 9:
Attach accessory to the syringe.

Step 10:
Push the plunger to dispense mixed biomaterial.

INJECTABLE AQUEOUS IMPLANT FORMULATION CONTAINING ASCORBIC ACID

CROSS-REFERENCE TO RELATED APPLICATIONS

The present application claims priority benefit of European Patent Application No. 19180283.4, filed on Jun. 14, 2019, the disclosure of which is incorporated herein by reference.

BACKGROUND

The invention relates to a new injectable aqueous implant formulation containing ascorbic acid and a process for preparing that new injectable aqueous implant formulation.

There are a number of risk factors for periodontal disease such as poor oral hygiene, tobacco smoking, diabetes, obesity, genetic disposition, age and socio-economic status that facilitate bacterial accumulation, biofilm formation and infection of the gingival sulcus and hence the formation of a gingival inflammation or gingivitis. If left untreated, the inflammation progresses along the tooth root and causes destruction of the PDL and the surrounding alveolar bone, which is then referred to periodontitis. As periodontal disease progresses, pockets develop between tooth and the soft tissue and continue to grow until the tooth loses its stability and may fall off. Clinical signs of periodontal disease are inflammation of soft tissues, bleeding on (tissue-) probing, possibly accompanied with suppuration, and radiographic loss of alveolar bone. A dentist can determine the presence and extent of periodontal disease using a probe to measure the depth of periodontal pockets, i.e. the depth between soft tissue or bone and the tooth, which is referred to the loss of clinical (tooth) attachment.

Guided Tissue Regeneration (GTR) is a widely used surgical procedure to treat the loss of periodontal structures. In this procedure, the periodontist obtains access to the diseased root and surrounding bone by incisions of the soft tissues to raise a flap. The next step is debridement of the diseased bone, soft tissues and the root surface by suitable hand instruments, ultrasonic or laser devices where diseased tissues are removed, and the root surface is scaled and planed. After debridement larger bone defects are filled with a bone regeneration material. Guided tissue regeneration barriers such as Geistlich Bio-Gide®, described in EP-B1-1676592 and commercially available from Geistlich Pharma AG, are placed over the bone regeneration material in deeper osseous defects. The periodontist closes the flap by appropriate sutures. Then, the gingiva, epithelial attachment, bone and periodontal attachment between the bone and tooth reform. While this procedure has been effective, incisions in the gingiva cause patient discomfort, pain, swelling, gingival recession, sensitive teeth, a long healing time and increase the possibility of re-infection.

Numerous natural and synthetic materials and compositions have been used as bone regeneration materials at the site of a bone defect.

A well-known natural, osteoconductive bone substitute material that promotes bone growth in periodontal osseous defects is Geistlich Bio-Oss®, commercially available from Geistlich Pharma AG. That material is manufactured from natural bone by a process described in U.S. Pat. Nos. 5,167,961 and 5,417,975, which enables preservation of the trabecular architecture and nanocrystalline structure of the natural bone, resulting in an excellent osteoconductive matrix which is not or very slowly resorbed.

To reduce the above-mentioned drawbacks related to incisions in the gingiva, there is a need for an injectable implant formulation.

For easy acceptance by patients when injected into periodontal pockets and convenient manual injection using a syringe, that injectable aqueous implant formulation should be extrudable through a cannula not larger in diameter than a gauge 18 (0.838 mm inner diameter) cannula or needle, preferably with a force not exceeding 60 N.

For optimal oral tissue regeneration, for regeneration of alveolar bone, root cementum or the periodontal ligament, it is desirable that the injected implant formulation provides a matrix of hydroxyapatite and collagen close to the natural in vivo environment in which such regeneration takes place.

Hydroxyapatite derived from natural bone is closer to the natural in vivo environment in which regeneration takes place than synthetic (non-biological) hydroxyapatite or ceramic.

Figure 5:
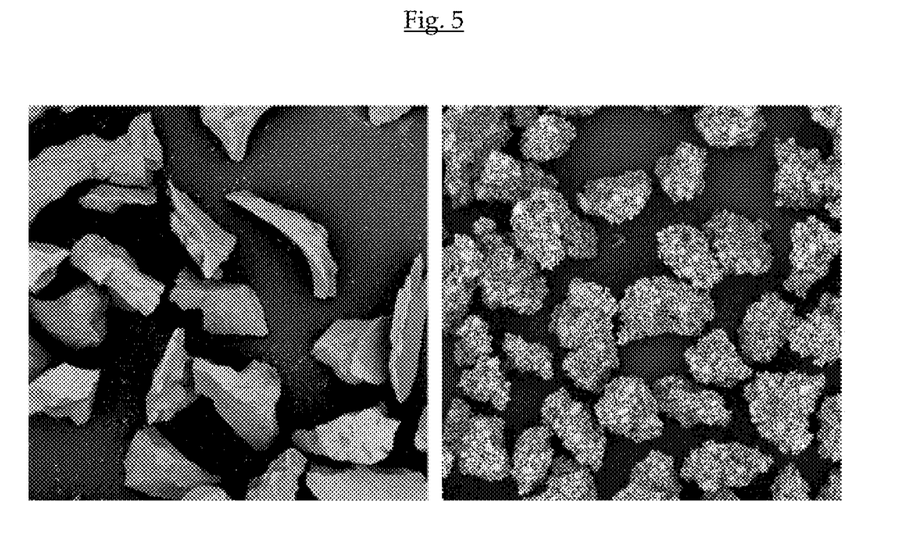
FIG. 5 represents on the left-hand-side a scanning electron micrograph (SEM) of nanocrystalline hydroxyapatite particles derived from natural bone and on the right-hand-side a SEM of synthetic beta-TCP particles.

Particles that are obtained by grinding hydroxyapatite derived from natural bone have a more irregular and longitudinal shape than the rounded particles obtained by grinding synthetic hydroxyapatite or ceramic: They thus present a higher risk of clogging a gauge 18 cannula. See FIG. 5 which represents on the left-hand-side a scanning electron micrograph (SEM) of nanocrystalline hydroxyapatite particles derived from natural bone and on the right-hand-side a SEM of synthetic beta-TCP particles. Results of extrusion through cannulae of formulations containing synthetic hydroxyapatite or ceramic particles are thus only partly predictive of extrusion of similar formulations containing hydroxyapatite particles derived from natural bone.

One important feature of human natural bone is the morphology and the very small size (nano-size) of the hydroxyapatite crystals, which for human bone mineral is: hexagonal space group $P6_3/m$, about 30 to 50 nm in length (c axis: [0,0,1]) and 14 to 25 nm in length (a and b axes: [1,0,0] and [0,1,0]). See Weiner, S. et al., 1992, FASEB, 6:879-885. To be closer to the natural environment in which regeneration takes place it is thus desirable to use nanocrystalline hydroxyapatite particles derived from natural bone, preferably with a morphology and size of crystals close to those of human natural bone.

US2012/0107401 describes flowable implantable osteoconductive matrices that comprise a mixture of 0.1-2 mm mineral particles of either ceramic such as synthetic hydroxyapatite and beta-TCP or hydroxyapatite derived from natural bone, collagen that can be soluble collagen or insoluble collagen derived from a human or animal source, and a therapeutic agent including a statin. Those flowable implantable osteoconductive matrices are taught to be suitable as putties or as gels that can be injected, sprayed or instilled to the target tissue site. The w/w ratio of ceramic to collagen is taught to be 0.15 to 22.5 (claims 4) or 1.5 to 11.5 (claim 5), the only specific ratios of ceramic to collagen disclosed being 5 and 4.83 (claims 2 and [0089], [0090]).

U.S. Pat. No. 7,322,825 discloses a method of treating periodontal disease by injection into periodontal pockets of a composition which is a mixture of finely ground bone particles of microcrystalline hydroxyapatite having a size of 50 to 400 µm and "free collagen" particles of less than 1 mm in diameter, those "free collagen" particles being taught to be non-crosslinked collagen small fibrils or gel containing fibrillar collagen and optionally a physiologically compatible thickener. That mixture only has a low enough viscosity to pass through an 18 gauge (0.838 mm inner diameter)

needle, after an additional energy infusion by application of heat, e.g. through microwave radiation. According to that patent, crosslinked collagen such as Avitene or Collastat cannot be cut in pieces small enough to go through an 18-gauge needle. For specifically described compositions, the w/w ratio of hydroxyapatite to collagen is 0.5 to 1.5.

The method of treating periodontal disease of U.S. Pat. No. 7,322,825 has not met wide-spread use. Non-crosslinked collagen such as "free collagen" is far from a natural in vivo environment that is desirable for oral tissue regeneration, for regeneration of alveolar bone, root cementum or the periodontal ligament.

U.S. Pat. No. 5,352,715 discloses an injectable ceramic formulation for soft and hard tissue repair and augmentation which comprises collagen and calcium phosphate ceramic particles in a pharmaceutically acceptable fluid carrier, wherein the calcium phosphate ceramic particles have a size of 50 to 250 μm and the w/w ratio of the phosphate ceramic particles to collagen is from 1/19 to 1/1, preferably from 1/4 to 1/2. According the teaching of that patent, calcium phosphate ceramic particles are preferably sintered ceramic particles of non-biological (synthetic) origin and the collagen is substantially free from crosslinking, i.e. deprived of telopeptides, the preferred collagen being a purified atelopeptide reconstituted collagen. That injectable ceramic formulation can pass through a 20 gauge (0.603 mm inner diameter) needle.

A combination of telopeptide deprived collagen and synthetic calcium phosphate particles is far from the natural in vivo environment in which regeneration takes place.

EP-0270254-A2 discloses a dried implant composition comprising a mixture containing, by weight exclusive of moisture, 2-40% of reconstituted fibrillary atelopeptide collagen which is substantially free from crosslinking and 60-98% of a tricalcium phosphate such as hydroxyapatite with a size range 100-2000 μm, the mass ratio of tricalcium phosphate to atelopeptide collagen being thus from 1.5 to 49. That dried implant composition is treated with gamma radiation to improve both biological and handling properties.

A combination of collagen deprived of telopeptides and synthetic tricalcium phosphate particles is far from the natural in vivo environment in which regeneration takes place.

The problem or objective of the invention of international PCT patent application WO-2019/115795 is to find a dried implant composition that can be used to prepare an injectable aqueous implant formulation for use in oral tissue regeneration, in particular regeneration of alveolar bone, root cementum or the PDL, that injectable aqueous implant formulation being extrudable through a tapering system and a gauge 18 cannula and not having the drawbacks of the implant formulations of the prior art.

By varying the methods of preparation, the components and the proportions of components in more than 300 prototypes of dried implant compositions comprising nanocrystalline hydroxyapatite particles derived from natural bone and naturally crosslinked fibrous collagen and submitting the formulations obtained by rehydration and homogeneous mixing of the dried implant compositions to an extrusion test using a gauge 18 cannula (described in Example 9), the inventors have found features of those dried implant compositions that unexpectedly provide extrudability through a tapering system and a gauge 18 cannula of the rehydrated and homogeneously mixed aqueous implant formulations, the latter providing a matrix close to the natural environment in which regeneration takes place.

That above objective is attained by the invention as defined in the claims of international PCT patent application WO-2019/115795.

The invention of that patent application concerns:
- a dried implant composition consisting essentially of a mixture of nanocrystalline hydroxyapatite particles derived from natural bone having a size of 50 to 200 μm as determined by sieving and fragments of a naturally crosslinked fibrous collagen material that pass through a 0.5 mm sieve, whereby the w/w ratio of nanocrystalline hydroxyapatite to collagen is from 1.8 to 4.5,
- the use of that dried implant composition for preparing by rehydrating and homogeneous mixing of 25-45 w/w % of the above dried implant composition with a pharmaceutically acceptable aqueous vehicle, an injectable aqueous implant formulation for use in oral tissue regeneration that is extrudable through a tapering system and a gauge 18 (0.838 mm inner diameter) 25.4 mm long cannula, and
- an injectable aqueous implant formulation for use in oral tissue regeneration which can be extruded through a tapering system and an 18 gauge (0.838 mm inner diameter) 25.4 mm long cannula with a force not exceeding 60 N, which comprises 25-45 w/w % of the above dried implant composition rehydrated and homogeneously mixed with sterile water or a sterile isotonic saline solution.

The term "consists essentially of a mixture of . . . " means that a very high proportion, usually at least 99% by weight of the dried implant consists of the recited mixture and at most 6% of a mineral salt, such as e.g. sodium chloride, the other components, usually at most 1% by weight of the dried implant, being derived from a natural source and not significantly affecting the extrusion behavior of the injectable aqueous implant formulation. Such components might be fat, sulfated ash, glucosamine, galactosamine and parts of residual proteins in very small quantities such as periostin, decorine and lumican or similar proteins. The other components do not include any synthetic polymer, any polyethylene oxide, any polypropylene oxide, or any synthetic lubricant. The other components do not include any statin or any artificial hydroxyapatite, i.e. hydroxyapatite of non-biological origin.

The "nanocrystalline hydroxyapatite particles derived from natural bone" are particles derived from natural bone by a process enabling preservation of the nanocrystalline structure of the natural bone. Such a process must be performed at a temperature sufficiently low such that there is no recrystallization of the mineral part of natural bone, usually a temperature not exceeding 700° C.

A suitable such process is disclosed in U.S. Pat. No. 5,167,961 or 5,417,975: It involves degrading organic matter in degreased bone by heating with ammonia, extracting the solubilized degradation products by washing with flowing water at temperatures below 60° C. and treating the bone mineral in air at temperatures between 250° C. and 600° C., such as to enable preservation of the trabecular structure and nanocrystalline structure of natural bone, giving nanocrystalline hydroxyapatite with a very low organic impurity or protein content. The nanocrystalline hydroxyapatite particles derived from natural bone may be obtained by grinding and sieving the above nanocrystalline hydroxyapatite.

The nanocrystalline hydroxyapatite particles derived from natural bone may also conveniently be obtained by grinding and sieving Geistlich Bio-Oss® Small Granules (available from Geistlich Pharma AG, CH-6110, Switzerland).

The "nanocrystalline hydroxyapatite particles derived from natural bone" suitable for incorporation into the composition of the invention have a size of 50 to 200 µm as determined by sieving.

Indeed, when the nanocrystalline hydroxyapatite particles derived from natural bone have a size over 200 µm, the implant formulation obtained by rehydration and homogeneous mixing tends to clog syringe cannulas of gauge 18 (0.838 mm inner diameter) and when the nanocrystalline hydroxyapatite particles derived from natural bone have a size below 50 µm, there is an increased risk of inflammation caused by those small particles.

The range size of 50 to 200 µm (as determined by sieving, see Example 1) is thus critical.

Preferably those nanocrystalline hydroxyapatite particles derived from natural bone have a size of 100 to 180 µm (as determined by sieving, see Example 1). The risks of inflammation or clogging are then minimized.

The term "naturally crosslinked fibrous collagen material" means fibrous collagen material derived from a natural tissue material by a process allowing to retain its telopeptide structure and most of its natural crosslinking. Such naturally crosslinked fibrous collagen material is an insoluble collagen material that has not been submitted to any enzyme treatment, any chemical crosslinking or any physical crosslinking (such as e.g. by DeHydroThermal treatment DHT, UV irradiation etc....). Indeed, any of the latter treatments may significantly change the telopeptide structure and/or the natural crosslinking present in the natural tissue material.

The naturally crosslinked fibrous collagen material is suitably derived from tissues of natural origin which contain 50 to 100 w/w % collagen and 0 to 50 w/w % elastin, preferably 70 to 95 w/w % collagen and 5 to 30% w/w elastin, as measured by desmosine/isodesmosine determination according to a modification of a known method involving hydrolysis and RP-HPLC (see e.g. Guida E. et al. 1990 *Development and validation of a high performance chromatography method for the determination of desmosines in tissues* in Journal of Chromatography or Rodriguqe P 2008 *Quantification of Mouse Lung Elastin During Prenatal Development* in The Open Respiratory Medicine Journal). Examples of such tissues include vertebrate, in particular mammalian (e.g. porcine, bovine, equine, ovine, caprine, lapine) peritoneum or pericardium membrane, placenta membrane, small intestine submucosa (SIS) and dermis. Such tissues are preferably porcine, bovine or equine. Interesting tissues are porcine, bovine or equine peritoneum membrane and dermis.

Preferably the naturally crosslinked fibrous collagen material is selected from the group consisting of porcine dermis and porcine peritoneum or pericardium membrane.

Usually the collagen is predominantly collagen type I, collagen type III or a mixture thereof. The collagen may also include a proportion of notably collagen type II, type IV, type VI or type VIII or any combination of those or any collagen types.

Usually the naturally crosslinked fibrous collagen material contains 50 to 100 w/w % collagen and 0 to 50 w/w % elastin, preferably 70 to 95 w/w % collagen and 5 to 30% w/w elastin.

A suitable naturally crosslinked fibrous collagen material derived from a natural tissue is a collagen membrane from porcine, bovine or equine peritoneum or pericardium prepared by a process similar to that described in "Example" of EP-B1-1676592, comprising an alkaline treatment, an acid treatment and a treatment by organic solvents, followed by mincing into fragments that go through a 0.5 mm sieve.

Another suitable naturally crosslinked fibrous collagen material derived from a natural tissue is the Geistlich Bio-Gide® (commercially available from Geistlich Pharma AG) that has been minced into fragments that go through a 0.5 mm sieve.

Another suitable naturally crosslinked fibrous collagen material derived from a natural tissue is porcine dermis prepared by a process similar to that described in Example 7 of EP-B1-2654816, comprising an alkaline treatment, an acid treatment, freeze-drying and cleaning by organic solvents, followed by mincing into fragments that go through a 0.5 mm sieve.

It is interesting that the naturally crosslinked fibrous collagen material includes mature collagen fibres showing triple helicity as shown by Circular Dichroism Spectroscopy. Such fibres indeed form a scaffold that favours colonization by oral tissue regeneration cells, in particular cells for regeneration of bone and cells for regeneration of the PDL.

The naturally crosslinked fibrous collagen material must be present in fragments that pass through a 0.5 mm sieve. Such fragments are generally obtained by milling the naturally crosslinked fibrous collagen by a procedure involving a centrifugal mill and sieving of the collagen fragments.

The feature of the naturally crosslinked fibrous collagen material of being present in fragments that pass through a 0.5 mm sieve is critical for extrusion through a tapering system and a gauge 18 (0.838 mm inner diameter) cannula. Indeed, as shown by experiments performed on numerous prototypes, when larger fragments of the naturally crosslinked material, e.g. fragments that go through a 0.6 or 0.7 mm sieve are used in the dried implant composition, there is a substantial risk of the implant formulation obtained by rehydration and homogeneous mixing of the dried implant composition clogging the gauge 18 cannula.

The w/w ratio of nanocrystalline hydroxyapatite to collagen is another critical parameter for extrusion through a tapering system and a gauge 18 (0.838 mm inner diameter) cannula.

Indeed, as shown by experiments performed on numerous prototypes, when the w/w ratio of nanocrystalline hydroxyapatite to collagen is below 1.8 or above 4.5, the implant formulation obtained by rehydration and homogeneous mixing is not readily injectable, the force required for extrusion through a tapering system and a gauge 18 (0.838 mm inner diameter) cannula being too high. This is an unexpected result for which there seems to be no straightforward explanation. The force required for extrusion steeply increases from 1.8 to 1.5 but only moderately increases from 4.5 to 6. However, as shown by experiments performed on numerous prototypes, when the ratio is more than 4.5, e. g. 5, reproducibility of the force required for extruding the implant formulation is not sufficient. The high reproducibility required for a commercial implant product is attained only when the ratio of nanocrystalline hydroxyapatite to collagen is from 1.8 to 4.5.

The range of the w/w ratio of nanocrystalline hydroxyapatite to collagen from 1.8 to 4.5 is thus critical.

Preferably the w/w ratio of nanocrystalline hydroxyapatite to collagen is from 2.5 to 4.2. Within that range the force required for extrusion is usually smaller.

Most preferably the w/w ratio of nanocrystalline hydroxyapatite to collagen is from 2.5 to 4.0. The highest reproducibility of the extrusion results with a small force has indeed been found for injectable aqueous implant formulations with that w/w ratio of nanocrystalline hydroxyapatite to collagen.

For enhancing extrudability of the injectable aqueous implant formulation it is suitable that the dried implant composition has been sterilized by gamma- or X-ray irradiation, using the usual radiation doses for sterilization, typically 27-33 kGy. Such a treatment indeed breaks certain bonds in the naturally crosslinked fibrous collagen and thus favors its flowability and extrudability.

The term "injectable aqueous implant formulation" refers to the implant formulation prepared by rehydration and homogeneous mixing of 25-45 w/w % of the dried implant composition with a pharmaceutically acceptable aqueous vehicle, which is capable of being conveniently injected into the human or animal body for oral tissue regeneration, in particular in periodontal pockets, being extrudable through a tapering system and gauge 18 (0.838 mm inner diameter) 25.4 mm long cannula.

Usually the injectable aqueous implant formulation is extrudable through a tapering system and gauge 18 (0.838 mm inner diameter) 25.4 mm long cannula with a force not exceeding 60 N.

Generally, that pharmaceutically acceptable aqueous vehicle is sterile water, a sterile isotonic saline solution, blood or fractions thereof, usually the patient's own blood.

The injectable aqueous implant formulation is preferably obtained by rehydration and homogeneous mixing of 25-45 w/w % of the dried implant composition, more preferably 30-40 w/w % of the dried implant composition, with sterile water, a sterile isotonic saline solution or blood. When using that quantity of the dried implant composition, the injectable aqueous implant formulation is a new formulation that is extrudable from a syringe through a tapering system and an 18 gauge (0.838 mm inner diameter) 25.4 mm long cannula with a force not exceeding 60 N.

When the injectable aqueous implant formulation is obtained by rehydration and homogeneous mixing of 30-40 w/w % of the above defined dried implant composition with sterile water or sterile isotonic saline solution, the force necessary to extrude the injectable aqueous implant formulation through a tapering system and an 18 gauge (0.838 mm inner diameter) 25.4 mm long cannula is below 40 N, preferably below 20 N.

When the injectable aqueous implant formulation is obtained by rehydration and homogeneous mixing of 30-40 w/w % of the above defined dried implant composition with blood, the force necessary to extrude the injectable aqueous implant formulation containing 30-40 w/w % of the dried implant composition in a pharmaceutically acceptable vehicle is below 45 N, preferably below 25 N. The dried implant composition used in the invention of international PCT patent application WO-2019/115795 may be prepared by a process comprising the following steps:

(a) Providing nanocrystalline hydroxyapatite particles derived from natural bone having a size of 50 to 200 µm as determined by sieving,
(b) Preparing milled naturally crosslinked fibrous collagen material by a process comprising an alkaline treatment, an acid treatment and a treatment by organic solvents, and mincing into fragments that pass through a 0.5 mm sieve,
(c) Adding the milled naturally crosslinked fibrous collagen material obtained in (b) to an aqueous solution, vigorously mixing such as to obtain a collagen slurry, adding the nanocrystalline hydroxyapatite particles having a size of 50 to 200 µm as determined by sieving prepared in (a) and vigorously mixing, the pH remaining from 4.2 to 7.5,
(d) Drying the mixed composition containing nanocrystalline hydroxyapatite particles and collagen obtained in (c) and
(e) Sterilizing by gamma- or X-ray irradiation the dried implant composition obtained in (d).

The nanocrystalline hydroxyapatite particles of ceramic derived from natural bone are particles derived from natural bone by a process enabling preservation of the nanocrystalline structure of the natural bone, as described above.

The high purity bone mineral obtained by the above process may be ground and sieved such as to have the required size.

Alternatively, particles of ceramic derived from natural bone having the required size may be produced from Geistlich Bio-Oss® commercially available from Geistlich Pharma AG) using grinding and sieving steps.

The milled naturally crosslinked fibrous collagen of step (b) may be prepared by a process similar to that described in Example 7 of EP-B1-2654815, which comprises grinding in water porcine, bovine, equine, caprine or lapine hides to pieces of 0.5 to 30 mm, removing the water using a water soluble solvent such as an alcohol or ketone, defatting using a chlorinated hydrocarbon such as dichloroethane or methylene chloride or a non-chlorinated hydrocarbon such as hexane or toluene, treating the collagen with a strong inorganic base at a pH above 12.0 and with a strong inorganic acid at a pH of 0 to 1, freeze-drying and cleaning the dry collagen fibres of the sponge obtained by organic solvents such as alcohols, ethers, ketones and chlorinated hydrocarbons, removing the solvents under vacuum, and further mincing the cleaned collagen sponge into fragments that go through a 0.5 mm sieve by a procedure involving a centrifugal mill and sieving of the collagen fragments.

The milled naturally crosslinked fibrous collagen of step (b) may also be prepared by a process similar to that described in EP-B1-1676592, which comprises freeing from flesh and grease by a mechanical treatment porcine, bovine, equine, peritoneum or myocardium membranes, washing with water, treating with a 1-5% sodium hydroxide solution, washing with water, acidifying with 0.2-0.8% hydrochloric acid, washing with water until a pH 3.5, neutralizing with a $NaHCO_3$ solution, washing with water, dehydrating with a water soluble solvent such as an alcohol or ketone, degreasing with an hydrocarbon such as hexane, and further mincing the cleaned collagen membranes into fragments that go through a 0.5 mm sieve by a procedure involving a centrifugal mill and sieving of the collagen fragments.

In step (c) the milled naturally crosslinked fibrous collagen prepared in step (b) is added to an aqueous solution and vigorously mixed such as to obtain a collagen slurry, then nanocrystalline hydroxyapatite particles having a size of 50 to 200 µm as determined by sieving prepared in step (a) are added to and vigorously mixed with the collagen slurry.

Usually the pH measured in step (c) is from 4.2 to 7.5, preferably from 4.5 to 7.5.

Step (d) generally comprises drying the mixed composition containing nanocrystalline hydroxyapatite particles and collagen obtained in (c) by freeze-drying or air drying preferably under reduced pressure.

The water content of the dried implant composition obtained in step (b) is generally 3-7% as measured by Karl Fischer titration.

Step (d) is optionally followed by step (e) of sterilization by gamma- or X-ray irradiation, generally using the usual radiation doses for sterilization, typically 27-33 kGy.

The invention international PCT patent application WO-2019/115795 further relates to a new injectable aqueous implant formulation for use in oral tissue regeneration which can be extruded through a tapering system and an 18 gauge (0.838 mm inner diameter) 25.4 mm long cannula with a force not exceeding 60 N, which comprises 25-45 w/w % of the above dried implant composition rehydrated and homogeneously mixed with sterile water or a sterile isotonic saline solution.

When the injectable aqueous implant formulation comprises 30-40 w/w % of the above dried implant composition rehydrated and homogeneously mixed with sterile water or a sterile isotonic saline solution, the force necessary to extrude the injectable aqueous implant formulation through a tapering system and an 18 gauge 1(0.838 mm inner diameter) 25.4 mm long cannula, is below 40 N, frequently below 20 N.

It has been observed that bone forming cells can grow in vitro in the injectable aqueous implant formulation of the invention. This shows the high biocompatibility of that injectable aqueous implant formulation which provides upon implantation a matrix very close to the natural in vivo environment in which regeneration takes place.

The above injectable aqueous implant formulation cannot be sterilized by gamma- or X-ray-irradiation while preserving its extrusion properties. Indeed, when that formulation is subjected to gamma- or X-ray-irradiation, free radicals are released which cause an uncontrolled crosslinking of the collagen, thereby causing the formulation to be non-extrudable through an 18 gauge (0.838 mm inner diameter) cannula or being extrudable through such a canula only using a force much too high to be applied manually.

SUMMARY OF THE INVENTION

It has now been found that when a sufficient amount of ascorbic acid has been added to above injectable aqueous implant formulation containing collagen, it can be sterilized by gamma-ray or X-ray-irradiation while preserving its extrusion properties: Ascorbic acid is consumed for scavenging the radicals released during sterilization by gamma-ray or X-ray-irradiation, thus avoiding uncontrolled crosslinking of collagen. Ascorbic acid should be added in excess compared to the amount that is expected to be consumed during such sterilization.

The sterilized injectable aqueous implant formulation which thus contains some residual ascorbic acid, generally at least 0.05% (w/w), can be extruded through a tapering system and an 18 gauge (0.838 mm inner diameter) 25.4 mm long cannula with the same force as the injectable aqueous implant formulation before sterilization. The sterilized injectable aqueous implant formulation retains those extrusion properties when stored at room temperature for a period of at least 9 months.

The invention thus concerns an injectable aqueous implant formulation which has been sterilized by gamma-ray or X-ray irradiation and which comprises 25-45 w/w % of a mixture of nanocrystalline hydroxyapatite particles derived from natural bone having a size of 50 to 200 μm as determined by sieving and fragments of naturally crosslinked fibrous collagen material that pass through a 0.5 mm sieve, whereby the w/w ratio of nanocrystalline hydroxyapatite to collagen is from 1.8 to 4.5, characterized in that it contains at least 0.05% (w/w) ascorbic acid.

The above sterilized injectable aqueous implant formulation retains those extrusion properties when stored at room temperature for a period of at least 9 months.

That injectable aqueous implant formulation remains stable, notably as regards its extrusion behavior, after storage at room temperature for a period of at least 9 months.

The injectable aqueous implant formulation may contain 0.1-1% (w/w) ascorbic acid. According to an embodiment, it contains 0.2-0.5% (w/w) ascorbic acid.

The w/w ratio of nanocrystalline hydroxyapatite to collagen is from 1.8 to 4.5. It may be from 2.5 to 4.2. According to an embodiment, it is from 2.5 to 4.0. According to an embodiment it is from 3.9 to 4.1.

The expression "particles having a size from x to y μm" as determined by sieving" means particles that pass through a sieve of "y μm" but are retained by a sieve of "x μm". The expression "nanocrystalline hydroxyapatite particles derived from natural bone is from 50 to 200 μm as determined by sieving" thus means "nanocrystalline hydroxyapatite particles derived from natural bone that pass through a 200 μm sieve but are retained by a 50 μm sieve". Selection of such particles having a size of 100 to 150 μm and a size of 125 to 180 μm as determined by sieving is illustrated in Example 11).

When using a laser method based on light scattering such as that described by M. Konert et al., 1997, Sedimentology 44: 523-535 for determining of the size of the nanocrystalline hydroxyapatite particles derived from natural bone, a substantially higher size would be measured due to the oblong/longitudinal form of such particles, far from the spheric form (see FIG. 5, left-hand side). For example, when using that a method for determining the size of such particles having a size of 125 to 180 μm as determined by sieving, results showed a mean value of 189.94 μm with 10% of the particles being over 281.87 μm.

The size of the nanocrystalline hydroxyapatite particles derived from natural bone is preferably from 100 to 180 μm as determined by sieving.

According to an embodiment, the size of the nanocrystalline hydroxyapatite particles derived from natural bone is from 125 to 180 μm as determined by sieving.

The term "naturally crosslinked fibrous collagen material" means fibrous collagen material derived from a natural tissue material by a process allowing to retain its telopeptide structure and most of its natural crosslinking. Such naturally crosslinked fibrous collagen material is an insoluble collagen material that has not been submitted to any enzyme treatment, any chemical crosslinking or any physical crosslinking (such as e.g. by DeHydroThermal treatment DHT, UV irradiation etc. . . . ). Indeed, any of the latter treatments may significantly change the telopeptide structure and/or the natural crosslinking present in the natural tissue material.

The naturally crosslinked fibrous collagen material is suitably derived from tissues of natural origin which contain 50 to 100 w/w % collagen and 0 to 50 w/w %) elastin, preferably 70 to 95 w/w % collagen and 5 to 30% w/w elastin, as measured by desmosine/isodesmosine determination according to a modification of a known method involving hydrolysis and RP-HPLC (see e.g. Guida E. et al. 1990 *Development and validation of a high performance chromatography method for the determination of desmosines in tissues in* Journal of Chromatography or Rodriguqe P 2008 *Quantification of Mouse Lung Elastin During Prenatal Development* in The Open Respiratory Medicine Journal). Examples of such tissues include vertebrate, in particular mammalian (e.g. porcine, bovine, equine, ovine, caprine, lapine) peritoneum or pericardium membrane, placenta membrane, small intestine submucosa (SIS) and dermis. Such tissues are preferably porcine, bovine or equine. Interesting tissues are porcine, bovine or equine peritoneum membrane and dermis.

Preferably the naturally crosslinked fibrous collagen material is selected from the group consisting of porcine dermis and porcine peritoneum or pericardium membrane.

Usually the naturally crosslinked fibrous collagen material contains 50 to 100 w/w % collagen and 0 to 50 w/w % elastin, preferably 70 to 95 w/w % collagen and 5 to 30% w/w elastin.

A suitable naturally crosslinked fibrous collagen material derived from a natural tissue is a collagen membrane from porcine, bovine or equine peritoneum or pericardium prepared by a process similar to that described in "Example" of EP-B1-1676592, comprising an alkaline treatment, an acid treatment and a treatment by organic solvents, followed by mincing into fragments that go through a 0.5 mm sieve.

Another suitable naturally crosslinked fibrous collagen material derived from a natural tissue is the Geistlich Bio-Gide® (commercially available from Geistlich Pharma AG) that has been minced into fragments that go through a 0.5 mm sieve.

Another suitable naturally crosslinked fibrous collagen material derived from a natural tissue is porcine dermis prepared by a process similar to that described in Example 7 of EP-B1-2654816, comprising an alkaline treatment, an acid treatment, freeze-drying and cleaning by organic solvents, followed by mincing into fragments that go through a 0.5 mm sieve.

The above defined injectable aqueous implant formulation which has been sterilized by gamma-ray or X-ray-irradiation can be extruded through a tapering system and an 18 gauge (0.838 mm inner diameter) 25.4 mm long cannula with a force not exceeding 60 N, e.g. using the extrusion test described in detail in Example 93). Such a force can be applied manually on a syringe. The same extrusion properties were found on that injectable aqueous implant formulation before sterilization.

Preferably the injectable aqueous implant formulation comprises 30-40 w/w % of a mixture of nanocrystalline hydroxyapatite particles derived from natural bone having a size of 50 to 200 μm as determined by sieving and fragments of naturally crosslinked fibrous collagen material that pass through a 0.5 mm sieve, whereby the w/w ratio of nanocrystalline hydroxyapatite to collagen is from 1.8 to 4.

The injectable aqueous implant formulation can then be extruded through a tapering system and an 18 gauge (0.838 mm inner diameter) 25.4 mm long cannula with a force not exceeding 30 N. Such a force can readily be applied manually on a syringe.

According to an embodiment, the injectable aqueous implant formulation comprises 29.5 to 30.5 w/w % of a mixture of nanocrystalline hydroxyapatite particles derived from natural bone having a size of 125 to 180 μm as determined by sieving and fragments of naturally crosslinked fibrous collagen material that pass through a 0.5 mm sieve, whereby the w/w ratio of nanocrystalline hydroxyapatite to collagen is from 1.8 to 4.5.

The injectable aqueous implant formulation can then be extruded through a tapering system and an 18 gauge (0.838 mm inner diameter) 25.4 mm long cannula with a force not exceeding 10 N. Such a force is convenient to apply manually on a syringe, even of a small size.

The invention also relates to a ready to use to use syringe containing the injectable aqueous implant formulation. Such a syringe is convenient to use in maxilla-facial operations for injecting through a 18-gauge cannula the above injectable aqueous implant formulation for use in oral tissue regeneration.

The invention also concerns a process for preparing the above injectable aqueous formulation, comprising adding fragments of naturally crosslinked fibrous collagen material that pass through a 0.5 mm sieve to sterile water or an isotonic solution and homogeneously mixing at an acidic pH at a temperature above 60° C. such as to produce a collagen slurry, adding to the collagen slurry nanocrystalline hydroxyapatite particles derived from natural bone such as to have a w/w ratio of nanocrystalline hydroxyapatite to collagen is from 1.8 to 4.5 and homogeneously mixing, adding 0.15 to 0.5% w/w of ascorbic acid and homogeneously mixing, and sterilizing by gamma-ray or X-ray irradiation.

The above injectable aqueous implant formulation may also be obtained by the process described in international PCT patent application WO-2019/115795, which comprises rehydrating and homogeneously mixing in sterile water or a sterile isotonic saline solution 25-45 w/w % of the dried implant composition consisting essentially of a mixture of nanocrystalline hydroxyapatite particles derived from natural bone having a size of 50 to 200 μm as determined by sieving and fragments of a naturally crosslinked fibrous collagen material that pass through a 0.5 mm sieve, whereby the w/w ratio of nanocrystalline hydroxyapatite to collagen is from 1.8 to 4.5, then adding 0.15 to 0.5% w/w of ascorbic acid and homogeneously mixing, and sterilizing by gamma-ray or X-ray irradiation.

Generally, sterilization by gamma-ray or X-ray irradiation is performed at 25-33 kGy.

The above ready to use syringe containing the injectable aqueous implant formulation is generally prepared by introducing into the syringe the above injectable aqueous formulation and carrying out sterilization by gamma-ray or X-ray irradiation on the filled syringe. The ready to use syringe is usable for a period of at least 9 months.

BRIEF DESCRIPTION OF THE DRAWINGS

The invention will be described in further detail with reference to illustrative examples of preferred embodiments of the invention and the accompanying figures in which.

DETAILED DESCRIPTION OF THE INVENTION

The following examples illustrate the invention without limiting its scope.

Example 1 Preparation of the Raw Materials

1) Preparation of Nanocrystalline Hydroxyapatite Fine Particles Having a Size of 100 to 150 μm or 125 to 180 μm as Determined by Sieving Nanocrystalline hydroxyapatite bone mineral fine particles were produced from cortical or cancellous bone as described in Examples 1 to 4 of U.S. Pat. No. 5,417,975, using an additional sieving step between 100 and 150 μm or 125 to 180 μm, respectively, i.e. selecting particles that pass through a 150 μm sieve but not through a 100 μm sieve or particles that pass through a 180 μm sieve but not through a 125 μm sieve, respectively.

Alternatively, nanocrystalline hydroxyapatite bone mineral fine particles were produced by grinding Geistlich Bio-Oss® Small Granules (available from Geistlich Pharma AG, CH-6110, Switzerland), careful impaction using a pistol and an additional sieving step between 100 and 150 μm (particles that pass through a 150 μm sieve but not through a 100 μm sieve) or 125 to 180 μm (particles that pass through a 180 μm sieve but not through a 125 μm sieve), respectively.

The above prepared nanocrystalline hydroxyapatite bone mineral fine particles having a size of between 100 and 150 μm, or 125 to 180 μm, as determined by sieving, were stored in glass bottles until use.

2) Preparation of Collagen A

Porcine hides were ground in a meat grinder to pieces of 1 to 20 mm. The water was removed using a water soluble solvent such as an alcohol or a ketone. The collagen fibres were defatted using a chlorinated hydrocarbon such as dichloroethane or methylene chloride or a non-chlorinated hydrocarbon such as hexane or toluene. After removing the solvent, the collagen was treated with a strong inorganic base at a pH above 12 for a period of 6 to 24 hours and treated with a strong inorganic acid at a pH of 0 to 1 for a period of 1 to 12 hours. The excess acid was removed by rinsing with water and the suspension was homogenized to a 0.5 to 2% homogenous suspension of collagen fibres in the presence of a swelling regulator such as an inorganic salt. The suspension was dried by freeze-drying and the dry collagen fibres of the sponge obtained was successively cleaned with different organic solvents such as alcohols, ethers, ketones and chlorinated hydrocarbons, the solvents being then evaporated under vacuum to a solvent residue of less than 1%.

1×1 cm pieces of the cleaned collagen sponge were cut by hand using scissors. The cut pieces were further minced by using first a cutting mill which includes a sieve of 0.5 to 4.0 mm, then a centrifugal mill (Retsch, ZM200) with a 0.5 mm sieve including trapezoid holes. The scissor cut pieces were alternatively milled directly with the centrifugal mill.

Collagen A consisting of naturally crosslinked fibrous collagen fragments that pass through a 0.5 mm sieve was thus obtained.

3) Preparation of Collagen B

The peritoneal membranes from young pigs were completely freed from flesh and grease by mechanical means, washed under running water and treated with 2% NaOH solution for 12 hours. The membranes were then washed under running water and acidified with 0.5% HCl. After the material had been acidified through its entire thickness (about 15 min) the material was washed until a pH of 3.5 was obtained. The material was then shrunk with 7% saline solution, neutralised with 1% $NaHCO_3$ solution and washed under running water. The material was then dehydrated with acetone and degreased with n-hexane.

The material was dried using ethanol ether and milled with a cutting mill (e.g. Pulverisette 25 from Fritsch: see www.fritsch.de./produkte/mahlen/schneidmuehlen/pulverisette-25 or SM300 from Retsch: www.retsch.de/de/produkte/zerkleinern/schneidmuehlen.htlm) which includes a trapezoidal sieve of 0.5 to 1.0 mm.

The cut collagen fibre segments were further minced by using a centrifugal mill (Retsch, ZM200) with a 0.5 mm sieve including trapezoid holes.

Collagen B consisting of naturally crosslinked fibrous collagen fragments that pass through a 0.5 mm sieve was thus obtained.

Example 2 Drying and Sterilization of Mixed Compositions Containing Nanocrystalline Hydroxyapatite Particles and Collagen The mixed compositions containing nanocrystalline hydroxyapatite particles and collagen (obtained as described in Examples 3 to 8 below) were dried by freeze-drying or air drying under reduced pressure and sterilized by gamma-ray or X-ray irradiation.

1) Freeze-Drying

From the 50 ml syringe the mass was filled up in 1 ml Cyclic Olefin Copolymer (COC) syringes from back side. Approximately 0.5 ml volume was filled up per 1 ml syringe. The syringes were stored closed from both sides for 5 hours in a fridge at 4° C. Then the syringes were opened on both sides and put on a metal plate in the lyophilisator, each syringe being in a lying down position such as have a large surface of contact with the metal plate. Then the following lyophilisation program was initiated:
1. Freezing in 7 hours to −40° C.
2. Holding 4 hours at −40° C.
3. Primary drying at −10° C. and 850 μbar during 20 hours
4. Secondary drying at +20° C. and 100 μbar during 6 hours Alternatively, the viscous collagen-nanocrystalline hydroxyapatite mass was not freeze-dried in syringes, but on stainless steel plates or in small stainless steel forms of less than 25 mm in diameter and less than 10 mm in depth. The dry obtained material after freeze drying was crushed into particles of 0.1 to 2 mm in size by using a centrifugal mill (Retsch, ZM200) with 1.5 mm up to 10 mm sieves. Crushing by a mill led to smaller nanocrystalline hydroxyapatite particles in the reconstituted end product.

Alternatively, for crushing the viscous collagen-nanocrystalline hydroxyapatite mass was extruded out of a standard luer outlet of a syringe and formed as straight lines on stainless steel plates. Then the material was freeze dried as such.

2) Air Drying

The viscous collagen-nanocrystalline hydroxyapatite mass e.g. formed as straight lines was alternatively dried by air in a vacuum oven at 30° C. and 10 mbar for 24 hours.

The dried straight lines were broken into 5 to 10 mm long sticks by hand.

The granulated material or the small sticks was then filled in a 3 ml syringe mixing system (MEDMIX, SP 003-00M-02/B, catalogue number 507211) with syringe cap with open bore luer and open bore cap (MEDMIX, CP 000-76M/D, catalogue number 506964).

3) Sterilization

The dried implant composition obtained by lyophilisation or air drying under reduced pressure was sterilized in the syringe by gamma-ray or X-ray irradiation with 27-33 kGy.

The water content in the dried product just after sterilisation was 3-7%, as measured by Karl Fisher titration.

The above steps of freeze-drying, air drying and sterilization by gamma-ray or X-ray irradiation on the dried implant solution were performed for dried implant compositions 1 to 6 prepared as described in Examples 3 to 8.

Example 3 Preparation of Dried Implant Composition 1 Containing Nanocrystalline Hydroxyapatite Particles Having a Size of 100 to 150 µm or 125 to 180 µm as Determined by Sieving and Collagen A, with a w/w Ratio of Nanocrystalline Hydroxyapatite to Collagen of 4.0

Preparation of the Collagen-Nanocrystalline Hydroxyapatite Composition Water and hydrochloric acid (2M) were mixed in a beaker with a spatula. The milled collagen A obtained in Example 1 was added and carefully pushed into the liquid to wet all the collagen. The beaker was closed with a screw lid and the water-collagen slurry was homogenously mixed by Speedmixer (CosSearch GmbH, Speedmixer DAC400.1FVZ) during 4 minutes with 2500 rpm. The collagen slurry was slightly heated up during the mixing procedure. Then the collagen slurry was cooled for 30 minutes in the fridge at 4° C.

The collagen slurry was mixed again by Speedmixer during 2 minutes with 2500 rpm. Then the nanocrystalline hydroxyapatite bone mineral fine particles having a size of between 100 and 150 µm, or 125 and 180 µm, as determined by sieving prepared in Example 1 were added in the beaker with the collagen slurry and the mass was mixed by Speedmixer during 2 minutes with 2000 rpm. The resulting pH was around 4.5.

The material quantities used in the experiments above are specified in the following table:

| Material | Net weight [g] |
| --- | --- |
| Water | 6.36 |
| HCl 2 mol/l | 0.64 |
| Collagen A | 0.60 |
| Hydroxyapatite particles 100-150 µm or 125-180 µm | 2.40 |

Drying of the Collagen-Nanocrystalline Hydroxyapatite Composition

Drying by freeze-drying or air drying under reduced pressure and sterilization was performed as described in Example 2.

Dried implant composition 1 containing nanocrystalline hydroxyapatite particles having a size of 100 to 150 µm or 125 to 180 µm as determined by sieving and collagen A with a w/w ratio of nanocrystalline hydroxyapatite to collagen of 4.0 and giving a pH of 4.5 after rehydration with demineralised water performed as described in Example 9, was thus obtained.

Example 4 Preparation of Dried Implant Composition 2 Containing Nanocrystalline Hydroxyapatite Particles Having a Size of 125 to 180 µm as Determined by Sieving and Collagen B, with a w/w Ratio of Nanocrystalline Hydroxyapatite to Collagen of 4.0

Preparation of the Collagen-Nanocrystalline Hydroxyapatite Composition

The milled collagen B obtained in Example 1 was carefully pushed into demineralized water to wet all the collagen. The beaker was closed with a screw lid and the water-collagen slurry was homogenously mixed by Speedmixer during 1 minute with 2500 rpm. The collagen slurry was then heated up to 70° C. in a water bath for 4 hours. Then the collagen slurry was cooled for 30 minutes at ambient temperature or in a fridge or in a water bath.

The collagen slurry was mixed again by Speedmixer during 2 minutes with 2500 rpm. Then the nanocrystalline hydroxyapatite bone mineral fine particles having a size of between 125 and 180 µm as determined by sieving prepared in Example 1 were added in the beaker with the collagen slurry and the mass was mixed by Speedmixer during 2 minutes with 2000 rpm. The resulting pH was 6.2.

The material quantities used in the experiments above are specified in the following table:

| Material | Net weight [g] |
| --- | --- |
| Water | 6.36 |
| Collagen B | 0.60 |
| Hydroxyapatite particles 125-180 µm | 2.40 |

Drying of the Collagen-Nanocrystalline Hydroxyapatite Composition

Drying by freeze-drying or air drying under reduced pressure and sterilization was performed as described in Example 2.

Dried implant composition 2 containing nanocrystalline hydroxyapatite particles having a size of 125 to 180 µm as determined by sieving and collagen B with a w/w ratio of nanocrystalline hydroxyapatite to collagen of 4.0 and giving a pH of 6.2 after rehydration with demineralised water performed as described in Example 9, was thus obtained.

Example 5 Preparation of Dried Implant Composition 3 Containing Nanocrystalline Hydroxyapatite Particles Having a Size of 125 to 180 µm as Determined by Sieving and a Mixture of 2 Parts of Collagen a for 1 Part of Collagen B, with a (w/w) Ratio of Nanocrystalline Hydroxyapatite to Collagen of 2.67

Preparation of the Collagen-Nanocrystalline Hydroxyapatite Composition

Water and hydrochloric acid (2M) were mixed in a beaker with a spatula. The milled Collagen B obtained in Example 1 was carefully pushed into the liquid to wet all the collagen. The beaker was closed with a screw lid and the water-collagen slurry was homogenously mixed by Speedmixer during 2 minutes with 2500 rpm with a resulting pH between 0.9 and 1. The collagen slurry was then heated up to 70° C.

in a water bath during 20 minutes. Then the collagen slurry was cooled down for 30 minutes in a water bath at 25° C.

The milled collagen A obtained in Example 1 was added and carefully pushed into the collagen slurry to wet all the collagen. Then the slurry was mixed by Speedmixer during 4 minutes with 2500 rpm.

Finally, the nanocrystalline hydroxyapatite bone mineral fine particles having a size of between 125 and 180 μm as determined by sieving prepared in Example 1 were added in the beaker with the collagen slurry and the mass was mixed by Speedmixer during 2 minutes with 2000 rpm. The resulting pH was around 4.5.

The material quantities used in the experiments above are specified in the following table:

| Material | Net weight [g] |
| --- | --- |
| Water | 6.08 |
| HCl 2 mol/l | 0.62 |
| Collagen A | 0.60 |
| Collagen B | 0.30 |
| Hydroxyapatite particles 125-180 μm | 2.40 |

Drying of the Nanocrystalline Hydroxyapatite-Collagen Composition

Drying by freeze-drying or air drying under reduced pressure and sterilization was performed as described in Example 2.

Dried implant composition 3 containing nanocrystalline hydroxyapatite particles having a size of 125 to 180 μm as determined by sieving and a mixture of 2 parts of collagen A for 1 part of collagen B, with a (w/w) ratio of nanocrystalline hydroxyapatite to collagen of 2.67, and giving a pH of 4.5 after rehydration with demineralised water performed as described in Example 9, was thus obtained.

Example 6 Preparation of Dried Implant Composition 4 Containing Nanocrystalline Hydroxyapatite Particles Having a Size of 125 to 180 μm as Determined by Sieving and a Mixture of 2 Parts of Collagen a for 1 Part of Collagen B, with a w/w Ratio of Nanocrystalline Hydroxyapatite to Collagen of 2.67

Preparation of the Collagen-Nanocrystalline Hydroxyapatite Composition

The milled Collagen B obtained in Example 1 was carefully pushed into demineralized water to wet all the collagen. The beaker was closed with a screw lid and the water-collagen slurry was homogenously mixed by Speedmixer during 1 minute with 2500 rpm. The collagen slurry was then heated up to 70° C. in a water bath during 20 min. Then the collagen slurry was cooled down for 30 minutes in a water bath at 25° C.

The milled collagen A obtained in Example 1 was added and carefully pushed into the collagen slurry to wet all the collagen. Then the slurry was mixed by Speedmixer during 4 minutes with 2500 rpm.

Finally, the nanocrystalline hydroxyapatite bone mineral fine particles having a size of between 125 and 180 μm as determined by sieving prepared in Example 1 were added in the beaker with the collagen slurry and the mass was mixed by Speedmixer during 2 minutes with 2000 rpm. The resulting pH was 6.0.

The material quantities used in the experiments above are specified in the following table:

| Material | Net weight [g] |
| --- | --- |
| Water | 6.70 |
| Collagen A | 0.60 |
| Collagen B | 0.30 |
| Hydroxyapatite particles 125-180 μm | 2.40 |

Drying of the Nanocrystalline Hydroxyapatite-Collagen Composition

Drying by freeze-drying or air drying under reduced pressure and sterilization was performed as described in Example 2.

Dried implant composition 4 containing nanocrystalline hydroxyapatite particles having a size of 125 to 180 μm as determined by sieving and a mixture of 2 parts of collagen A for 1 part of collagen B, with a w/w ratio of nanocrystalline hydroxyapatite to collagen of 2.67, and giving a pH of 6.0 after rehydration with demineralised water performed as described in Example 9, was thus obtained.

Example 7 Preparation of Dried Implant Composition 5 Containing Nanocrystalline Hydroxyapatite Particles Having a Size of 125 to 180 μm as Determined by Sieving and Collagen A, with a w/w Ratio of Nanocrystalline Hydroxyapatite to Collagen of 4.0

Preparation of the Collagen-Nanocrystalline Hydroxyapatite Composition

The milled Collagen A was carefully pushed into demineralized water to wet all the collagen. The nanocrystalline hydroxyapatite bone mineral fine particles having a size of between 125 and 180 μm as determined by sieving prepared in Example 1 were added and the beaker was closed with a screw lid. The water-collagen-nanocrystalline hydroxyapatite slurry was homogenously mixed by Vortex mixer during 1 minute and a scoop during 1 minute.

The resulting pH was 6.1.

The used material quantities are described in the following table:

| Material | Net weight [g] |
| --- | --- |
| Water | 7.0 |
| Collagen A | 0.60 |
| Hydroxyapatite particles 125-180 μm | 2.40 |

Drying of the Nanocrystalline Hydroxyapatite-Collagen Composition

Drying by freeze-drying or air drying under reduced pressure and sterilization was performed as described in Example 2.

Dried implant composition 5 containing nanocrystalline hydroxyapatite particles having a size of 125 to 180 μm as determined by sieving and collagen A, with a w/w ratio of nanocrystalline hydroxyapatite to collagen of 4.0, and giving a pH of 6.1 after rehydration with demineralized water performed as described in Example 9, was thus obtained.

Example 8 Preparation of Dried Implant Composition 6 Containing Nanocrystalline Hydroxyapatite Particles Having a Size of 125 to 180 µm as Determined by Sieving and Collagen A, with a (w/w) Ratio of Nanocrystalline Hydroxyapatite to Collagen A of 2.0

Preparation of the Collagen-Nanocrystalline Hydroxyapatite Composition

The milled Collagen A was carefully pushed into demineralized water to wet all the collagen. The nanocrystalline hydroxyapatite bone mineral fine particles having a size of between 125 and 180 µm as determined by sieving prepared in Example 1 were added and the beaker was closed with a screw lid. The water-collagen-nanocrystalline hydroxyapatite slurry was homogenously mixed by Vortex mixer during 1 minute and a scoop during 1 minute.

The resulting pH was 5.8.

The used material quantities are described in the following table:

| Material | Net weight [g] |
|---|---|
| Water | 7.0 |
| Collagen A | 1.0 |
| Bio-Oss 125-180 µm | 2.0 |

Drying of the Nanocrystalline Hydroxyapatite-Collagen Composition

Drying by freeze-drying or air drying under reduced pressure and sterilization was performed as described in Example 2.

Dried implant composition 6 containing nanocrystalline hydroxyapatite particles having a size of 125 to 180 µm as determined by sieving and collagen A, with a (w/w) ratio of nanocrystalline hydroxyapatite to collagen of 2.0, and giving a pH of 5.8 after rehydration with demineralised water performed as described in Example 9, was thus obtained.

Example 9 Preparation of a Ready-to-Use Syringe Containing an Injectable Aqueous Implant Formulation by Rehydration of the Dried Implant Composition in the Syringe 1) Preparation of a Ready to Use Syringe Containing an Injectable Aqueous Implant Formulation Obtained by Rehydration and Homogeneous Mixing of the Dried Implant Composition a) Using a 3-Way Stopcock Valve Luer-Lok Adapter and a 1 ml Syringe 2) Dried, sterile nanocrystalline hydroxyapatite-collagen compositions in the 1 ml product syringe were rehydrated by using a 3-way stopcock valve Luer (Luer-Lok) adapter (BD Connecta, 3-way stopcock, catalog number 394600), Vaclok syringes (Qosina, Vaclok syringe, catalog number C1097) and a normal single use supplementary syringe 1 ml (Luer-Lok).

The liquid to rehydrate the collagen was demineralised water, an isotonic saline solution, a PBS solution of pH 7.4 containing 150 mM sodium phosphate buffer (prepared by dissolving $NaH_2PO_4$ in demineralised water and adjusting the pH with sodium hydroxide), or blood.

The weight of the dry biomaterial (dried implant composition obtained in one of Examples 3 to 8) in the syringe was known or was measured. An amount of rehydrating liquid was filled in the supplementary syringe such as to obtain an injectable paste containing by weight 38% dry biomaterial.

The product syringe was then connected to the 3-way stopcock valve and the 180° counterpart of the 3-way stopcock valve was closed by a closing cap. At the third position (90° from the product syringe) of the 3-way stopcock valve a 60 ml Vaclok Syringe was connected to the system. Air was evacuated from the product syringe by pulling the plunger of the Vaclok Syringe and locking at 50 ml volume. Then the 3-way valve was rotated by 180° to keep the vacuum in the product syringe, whereas the Vaclok Syringe was replaced by the supplementary syringe filled with liquid. Then the 3-way valve was rotated by 180°. Due to the vacuum, the liquid automatically flowed into the product syringe and wetted the product. To ensure the complete liquid transfer into the product syringe the plunger of the product syringe was drawn back. The material was rested for 30 seconds to enable rehydration before the material was pushed from the product syringe into the supplementary syringe and back, this sequence repeated 40 times to obtain a homogeneously mixed material. After the mixing procedure the 3-way stopcock valve was replaced by the applicator which is a tapering system and a blunt end 18 gauge (inner diameter 0.838 mm) 25.4 mm long cannula.

The reconstituted injectable aqueous implant formulation obtained by rehydration and homogeneous mixing of each of the dried implant compositions 1 to 6 with demineralised water had a pH near to the pH measured before lyophilisation, namely about 4.5, 6.2, 4.5, 6.0, 6.1 and 5.8, respectively.

b) Using a 3 ml Medmix Syringe Mixing System

Figure 1:
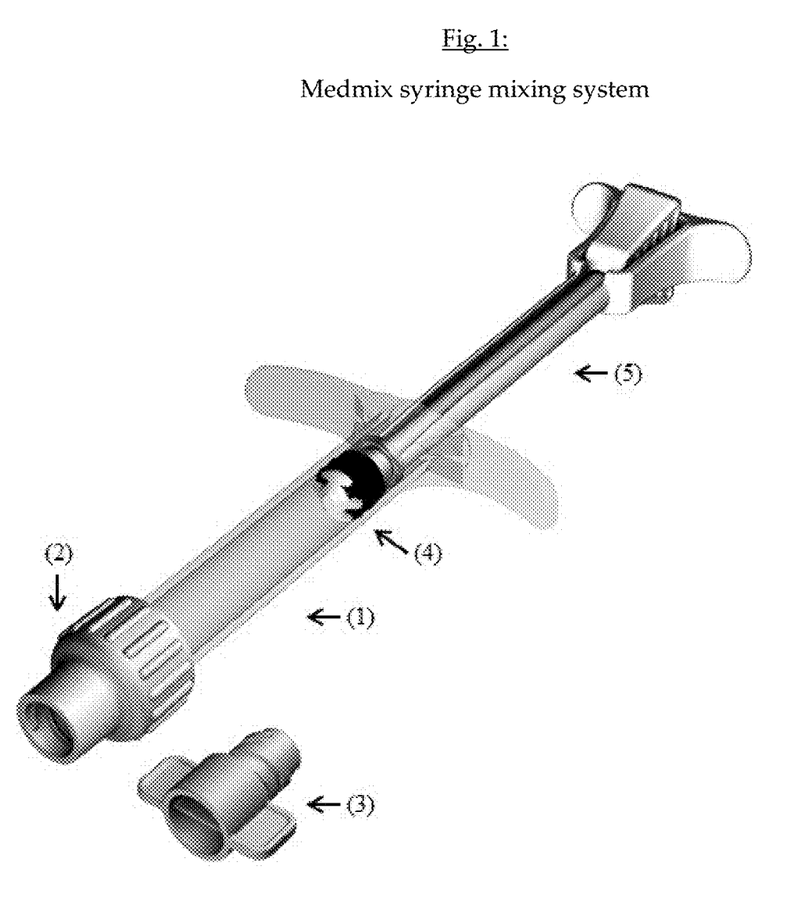
FIG. 1 represents the Medmix syringe mixing system (MEDMIX, SP 003-00M-02/B, catalogue number 507211), (1) being the syringe containing the dry biomaterial, (2) being the syringe cap with an open bore luer outlet, which is compatible with any luer cannula, (3) being the open bore cap to close the syringe during the mixing process, (4) being the mixing device, which is a flexible mixer once the plunger has been removed and (5) being the plunger, that can be removed to mix the material in the syringe and can be reset afterwards to push out the material.

Alternatively the particles of the dried material were rehydrated with demineralised water, an isotonic saline solution, a PBS solution of pH 7.4 containing 150 mM sodium phosphate buffer or blood, in the Medmix syringe mixing system (MEDMIX, SP 003-00M-02/B, catalog number 507211) with syringe cap with open bore luer and open bore cap (MEDMIX, CP 000-76M/D, catalog number 506964), represented in FIG. 1 in which (1) is the syringe containing the dry biomaterial, (2) is the syringe cap with an open bore luer outlet, which is compatible with any luer cannula, (3) is the open bore cap to close the syringe during the mixing process, (4) is the mixing device, which is a flexible mixer once the plunger is removed, (5) is the plunger, that can be removed to mix the material in the syringe and can be reset afterwards to push out the material.

Figure 2:
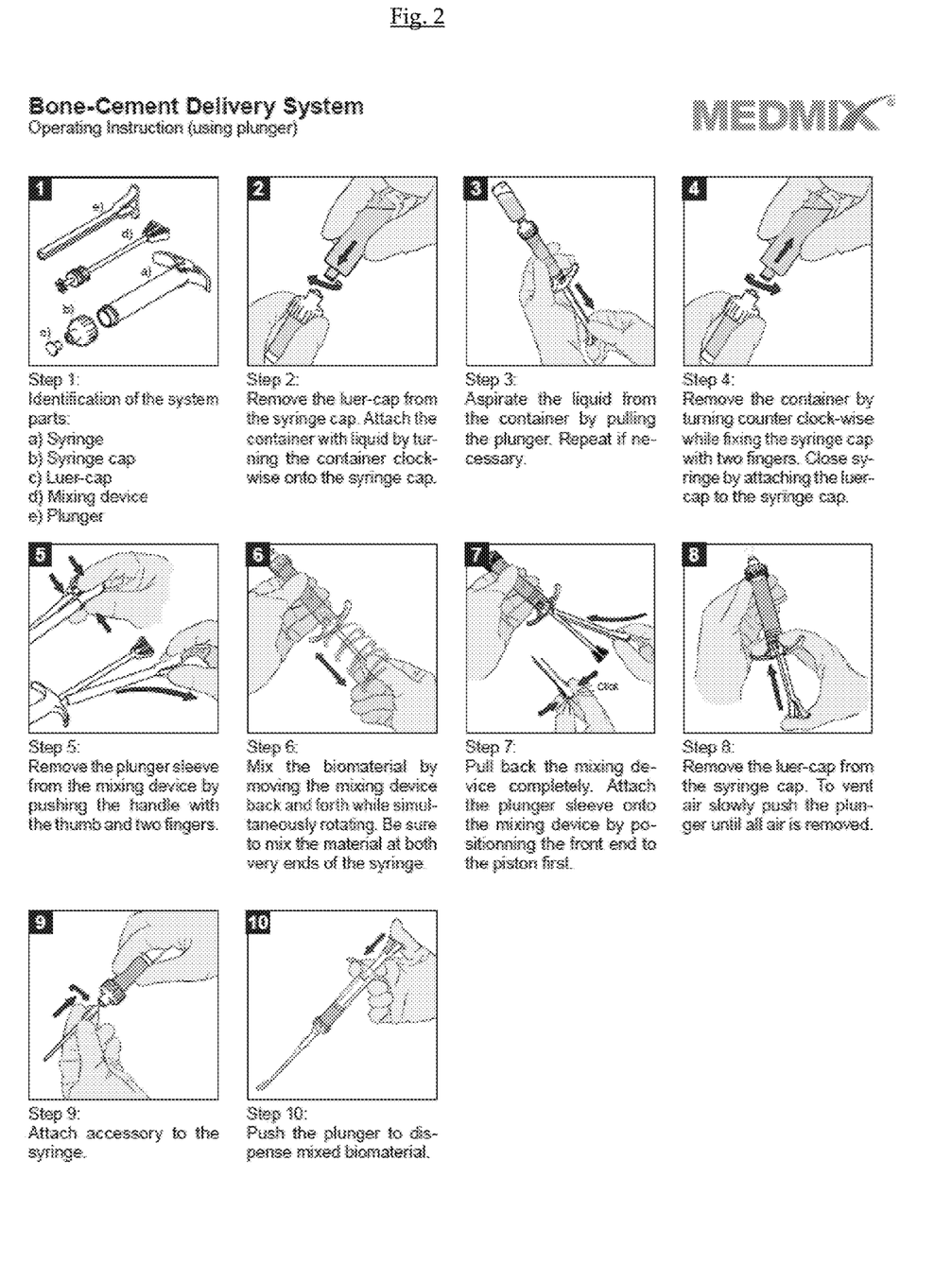
FIG. 2 is a copy of the Medmix mixing procedure as set out in the Operating Instruction which is attached to the Medmix syringe mixing system.

The Medmix mixing procedure set out in FIG. 2 was followed. To get an optimal result, after step 4 the plunger is pushed 3 times in order to push the liquid into the material to wet it and perform the mixing step (step 6) for 60 seconds. All the air is removed in step 8.

3) Extrusion Test

The extrudability of the reconstituted injectable aqueous implant formulation obtained was tested with a tension and pressure testing device (Zwick & Roell, BT1-FR2.5TS.D14). The ready to use syringe prepared above was placed vertically in a syringe holding and the plunger was pressed down from the machine while the force of pressing the product out of the syringe through the applicator comprising a tapering system and a blunt end 18 gauge (inner diameter 0.838 mm) 25.4 mm long cannula (Nordson EFD, Precision Tip 18GA 1", catalog number 7018110), was measured with the following program:
Force till resistance: 0.1 N
Speed till resistance: 100 mm/min
Testing speed: 1 mm/s, position controlled
End of testing: force limit, 150 N
Force sensor: 200 N For all tested injectable implant formulations obtained by rehydration and homogeneous mixing with demineralised water, an isotonic saline solution or a PBS solution, notably for injectable implant formulations, which were prepared from dried implant compositions 1 to 6, the measured force did not exceed 40 N.

For all tested injectable implant formulations obtained by rehydration and homogeneous mixing with blood, notably for injectable implant formulations, which were prepared from dried implant compositions 1 to 6, the measured force did not exceed 45 N.

For injectable implant formulations obtained by rehydration and homogeneous mixing with demineralised water, an isotonic saline solution or a PBS solution, which were prepared from dried implant compositions 1, 2, 3, 4, 5 and 6 the measured force did not exceed 20 N.

For injectable implant formulations obtained by rehydration and homogeneous mixing with blood, which were prepared from dried implant composition 1 (containing nanocrystalline hydroxyapatite particles having a size of 100 to 150 µm or 125 to 180 µm as determined by sieving and collagen A, with a w/w ratio of nanocrystalline hydroxyapatite to collagen of 4.0) and dried implant composition 2 (containing nanocrystalline hydroxyapatite particles having a size of 125 to 180 µm as determined by sieving and collagen B, with a w/w ratio of nanocrystalline hydroxyapatite to collagen of 4.0), the measured force did not exceed 25 N.

Figure 3A:
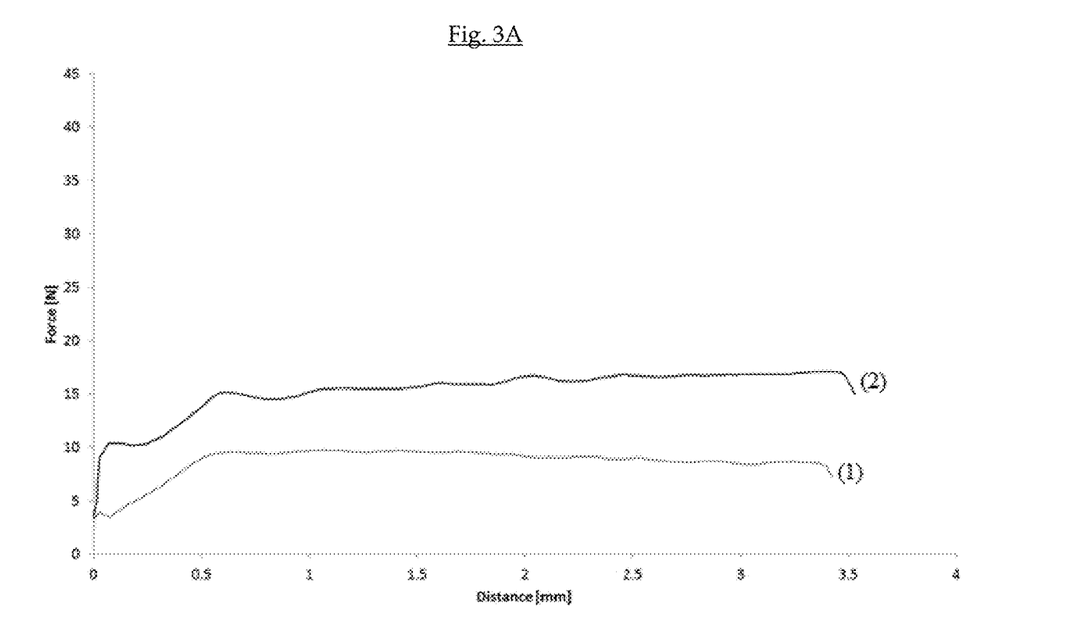
FIGS. 3A and 3B represent the extrusion curves of the injectable aqueous implant formulations obtained by rehydrating and homogeneously mixing dried implant compositions 2 and 4 in the examples with isotonic saline (curves (1) and (3)) or fresh human blood (curves (2) and (4)), respectively.
Figure 3B:
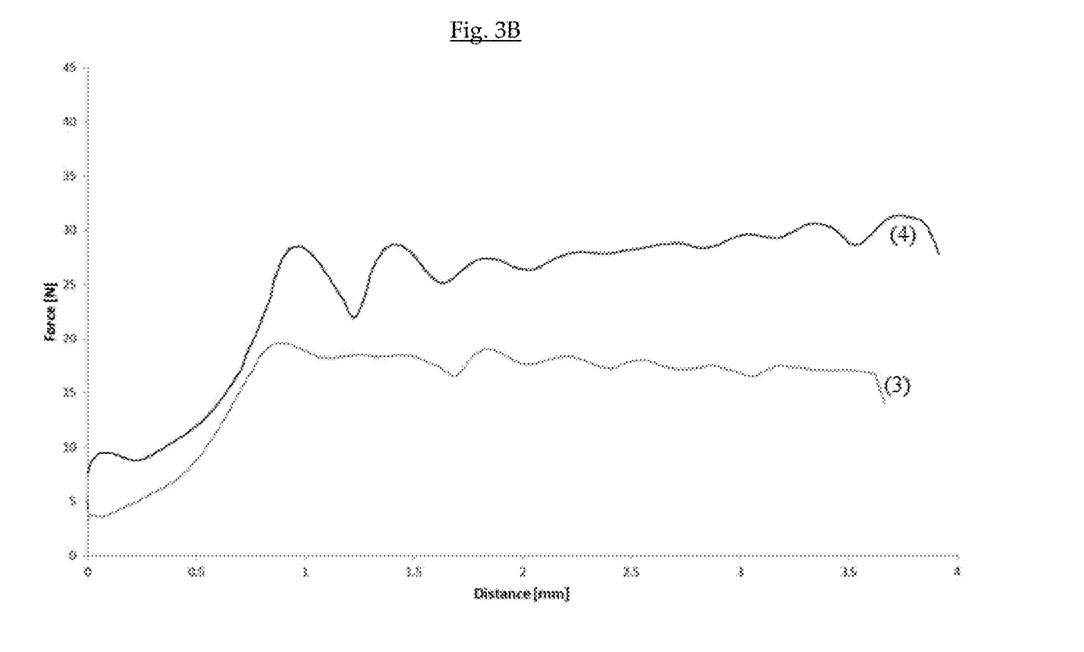
Figure 4:
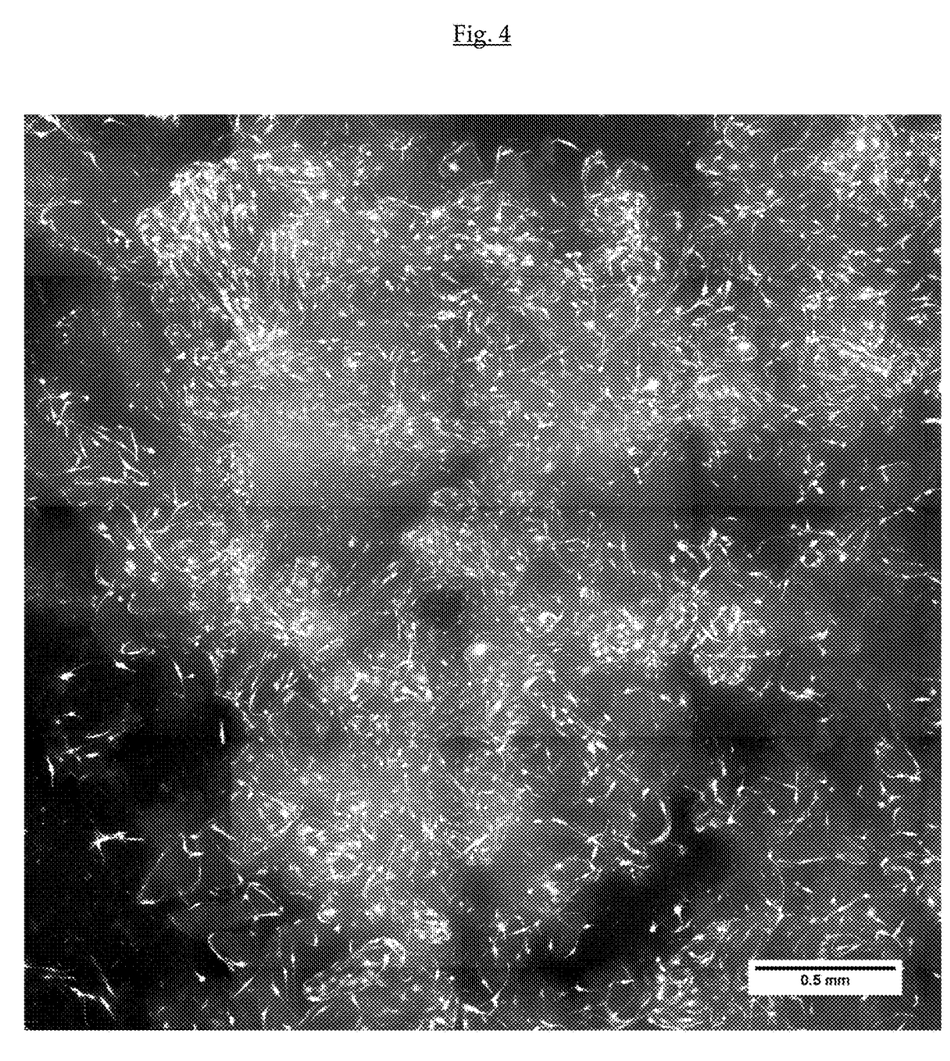
FIG. 4 is a microscopy image using a CV1000 confocal spinning disk microscope with excitation by 561 nm laser illumination of injectable aqueous implant formulation 4 obtained by rehydrating and homogeneously mixing dried implant composition 4 (prepared in Example 6) with human blood: the grown MC3T3 CytoLight Red cells are visualised in bright.

See FIGS. 3A and 3B, which represent the extrusion curves of the injectable implant formulations obtained by rehydrating and homogeneously mixing dried implant compositions 2 and 4 with isotonic saline or fresh human blood, respectively.

In FIG. 3A, (1) and (2) are the extrusion curves of dried implant composition 2 (containing nanocrystalline hydroxyapatite particles having a size of 125 to 180 µm as determined by sieving and collagen B, with a w/w ratio of nanocrystalline hydroxyapatite to collagen of 4.0) rehydrated with isotonic saline and fresh human blood, respectively.

In FIG. 3B, (3) and (4) are the extrusion curves of dried implant composition 4 (containing nanocrystalline hydroxyapatite particles having a size of 125 to 180 µm as determined by sieving and a mixture of 2 parts of collagen A for 1 part of collagen B, with a w/w ratio of nanocrystalline hydroxyapatite to collagen of 2.67) rehydrated with isotonic saline and fresh human blood, respectively.

Example 10 Preparation of an Injectable Aqueous Implant Formulation Containing 38% of a Mixture of Nanocrystalline Hydroxyapatite Particles Derived from Natural Bone Having a Size of 125 to 180 µm as Determined by Sieving and Collagen B, with a w/w Ratio of Ceramic to Collagen of 4.0, which Contains Ascorbic Acid The milled collagen B obtained in Example 1 was carefully pushed into demineralized water to wet all the collagen. The beaker was closed with a screw lid and the water-collagen slurry was homogenously mixed by Speedmixer (FlackTech Inc., USA) during 2 minutes with 2500 rpm. 5 drops of 2M hydrochloric acid was used to lower the pH. After an additional mixing step by Speedmixer during 2 minutes with 2500 rpm, the pH was measured with the aim to adjust the pH to 3.5. The collagen slurry was then heated up to 70° C. in a water bath for 4 hours. Then the collagen slurry was in a water bath at 25° C.

The collagen slurry was mixed again by Speedmixer during 2 minutes with 2500 rpm. Then the ceramic bone mineral fine particles having a size of between 125 and 180 µm as determined by sieving prepared in Example 1 were added in the beaker with the collagen slurry and the mass was mixed by Speedmixer during 3 minutes with 2000 rpm.

2.76 mg ascorbic acid per g of the mass (for experiment 1), 1.76 mg ascorbic acid per g of the mass (for experiment 2) or 1.33 mg ascorbic acid per g of the mass (for experiment 3) were dissolved in 0.1 ml water, added to the mass and mixed by Speedmixer during 1 minute with 2000 rpm, thereby giving an injectable aqueous implant formulation having a pH of 6.0.

The material quantities used in the experiments above are specified in the following table:

| Material | Net weight [g] |
| --- | --- |
| Water | 6.2 |
| Collagen B | 0.76 |
| Ceramic particles 125-180 µm | 3.04 |
| Ascorbic acid (Experiment 1) | 0.00264 |
| Ascorbic acid (Experiment 2) | 0.00176 |
| Ascorbic acid (Experiment 3) | 0.00133 |

Each of the above three injectable aqueous implant formulations (in the test described above in Example 9, 3)) could be extruded through a tapering system and an 18 gauge (0.838 mm inner diameter) 25.4 mm long cannula with a force not exceeding 30 N. Such a low force can conveniently be applied manually on a small syringe.

The resulting mass was packed into a 50 ml syringe from the backside using a spatula and filled into smaller 0.5 ml and 1.0 ml syringes. Then the filled syringes were stored at the fridge at 4° C. overnight, then stored and sterilized at ambient temperature by X-ray irradiation at 25-33 kGy within 3 days.

Shortly after sterilization, the injectable aqueous solution of experiment 1 or experiment 2 could be extruded through a tapering system and an 18 gauge (0.838 mm inner diameter) 25.4 mm long cannula with a force not exceeding 25 N. However, the injectable aqueous solution of experiment 3 could only be extruded with a force 40-45 N.

The residual ascorbic acid in the sterilized injectable aqueous solution of experiment 1 was determined to be about 1.20 mg/g, which showed that an amount of about 1.44 mg/g of initial 2.64 mg/g had been consumed during sterilization. The initial amount of 1.33 mg/g of the injectable aqueous solution of experiment 3 might thus not have been sufficient to scavenge enough free radicals released during its sterilization, thus leading to a slight crosslinking of the collagen, which would explain the higher force required for extrusion through a tapering system and an 18 gauge (0.838 mm inner diameter) 25.4 mm long cannula.

After being stored for 9 months in syringes at room temperature, the extrusion properties of each of the above sterilized injectable aqueous implant formulations were the same as reported above shortly after sterilization, namely extrudability with a force not exceeding 25 N for the sterilized injectable aqueous implant formulation of experiment 1 or 2 and with a force 40-45 N for the sterilized injectable aqueous implant formulation of experiment 3.

Example 11 Preparation of an Injectable Aqueous Implant Formulation Containing 30% of a Mixture of Nanocrystalline Hydroxyapatite Particles Derived from Natural Bone Having a Size of 125 to 180 μm as Determined by Sieving and Collagen B, with a w/w Ratio of Ceramic to Collagen of 4.0, which Contains Ascorbic Acid The milled collagen B obtained in Example 1 was carefully pushed into demineralized water to wet all the collagen. The beaker was closed with a screw lid and the water-collagen slurry was homogenously mixed by Speedmixer (FlackTech Inc., USA) during 2 minutes with 2500 rpm. 5 drops of 2M hydrochloric acid were used to lower the pH. After an additional mixing step by Speedmixer during 2 minutes with 2500 rpm, the pH was measured with the aim to adjust the pH to 3.5. The collagen slurry was then heated up to 70° C. in a water bath for 3 hours. Then the collagen slurry was in a water bath at 25° C.

The collagen slurry was mixed again by Speedmixer during 2 minutes with 2500 rpm. Then the ceramic bone mineral fine particles having a size of between 125 and 180 μm as determined by sieving prepared in Example 1 were added in the beaker with the collagen slurry and the mass was mixed by Speedmixer during 3 minutes with 2000 rpm. 1.76 mg ascorbic acid per g of the mass was dissolved in 0.1 ml water, added to the mass and mixed by Speedmixer during 1 minute with 2000 rpm, thereby giving an injectable aqueous implant formulation having a pH of 6.0.

The material quantities used in the experiments above are specified in the following table:

| Material | Net weight [g] |
| --- | --- |
| Water | 7.00 |
| Collagen B | 0.60 |
| Ceramic particles 125-180 μm | 2.40 |
| Ascorbic acid | 0.00176 |

The injectable aqueous implant formulation (in the test described above in Example 9, 3)) could be extruded through a tapering system and an 18 gauge (0.838 mm inner diameter) 25.4 mm long cannula with a force not exceeding 10 N. Such a low force can conveniently be applied manually on a small syringe.

The resulting mass was packed into a 50 ml syringe from the backside using a spatula and filled into smaller 0.5 ml and 1.0 ml syringes. Then the filled syringes were stored at the fridge at 4° C. overnight, then stored and sterilized at ambient temperature by X-ray irradiation at 25-33 kGy within 3 days.

Shortly after sterilization, the injectable aqueous solution could be extruded through a tapering system and an 18 gauge (0.838 mm inner diameter) 25.4 mm long cannula with a force not exceeding 10 N.

After being stored for 9 months in a syringe at room temperature, the extrusion properties of the above sterilized injectable aqueous implant formulations were the same as reported above before or shortly after sterilization.

The invention claimed is:

1. An injectable aqueous implant formulation which has been sterilized by gamma-ray or X-ray-irradiation and which comprises 25-45 w/w % of a mixture of nanocrystalline hydroxyapatite particles derived from natural bone having a size of 50 to 200 μm as determined by sieving and fragments of naturally crosslinked fibrous collagen material that pass through a 0.5 mm sieve, whereby the w/w ratio of nanocrystalline hydroxyapatite to collagen is from 1.8 to 4.5 and the injectable aqueous formulation comprises 0.1-1% (w/w) ascorbic acid.

2. The injectable aqueous implant formulation of claim 1, comprising 30-40 w/w % of the mixture of nanocrystalline hydroxyapatite particles.

3. The injectable aqueous implant formulation of claim 1, comprising 29.50 to 30.50 w/w % of the mixture of nanocrystalline hydroxyapatite particles.

4. The injectable aqueous implant formulation of claim 1, comprising 0.2-0.5% (w/w) ascorbic acid.

5. The injectable aqueous implant formulation of claim 1, wherein the w/w ratio of nanocrystalline hydroxyapatite to collagen is from 2.5 to 4.2.

6. The injectable aqueous implant formulation of claim 1, wherein the w/w ratio of nanocrystalline hydroxyapatite to collagen is from 2.5 to 4.0.

7. The injectable aqueous implant formulation of claim 1, wherein the w/w ratio of nanocrystalline hydroxyapatite to collagen is from 3.9 to 4.1.

8. The injectable aqueous implant formulation of claim 1, wherein the nanocrystalline hydroxyapatite particles have a size from 100 to 180 μm as determined by sieving.

9. The injectable aqueous implant formulation of claim 1, wherein the nanocrystalline hydroxyapatite particles have a size from 125 to 180 μm as determined by sieving.

10. The injectable aqueous implant formulation of claim 1, wherein the naturally crosslinked fibrous collagen material is selected from the group consisting of porcine dermis and porcine peritoneum or pericardium membrane.

11. A ready to use syringe containing the injectable aqueous implant formulation of claim 1.

12. A process for preparing the injectable aqueous implant formulation of claim 1, comprising
    a) adding fragments of naturally crosslinked fibrous collagen material that pass through a 0.5 mm sieve to a pharmaceutically acceptable aqueous vehicle and homogeneously mixing at an acidic pH at a temperature above 60° C. to produce a collagen slurry,
    b) adding nanocrystalline hydroxyapatite particles prepared in (a) to the collagen slurry, whereby the w/w ratio of nanocrystalline hydroxyapatite to collagen is from 1.8 to 4.5 to form a HAP/collagen slurry and homogeneously mixing,
    c) adding 0.1-1% w/w of ascorbic acid to the HAP/collagen slurry and homogeneously mixing to form an ascorbic acid/HAP/collagen slurry, and
    d) sterilizing the ascorbic acid/HAP/collagen slurry by gamma-ray or X-ray irradiation.

13. The process of claim 12, wherein sterilizing by gamma-ray or X-ray irradiation is performed at 25-33 kGy.

14. The injectable aqueous implant formulation of claim 1, wherein the formulation has properties such that it is extrudable through a tapering system and an 18 gauge (0.838 mm inner diameter) 25.4 mm long cannula with a force not exceeding 40 N.

15. The injectable aqueous implant formulation of claim 1, wherein the formulation has properties such that it is extrudable through a tapering system and an 18 gauge (0.838 mm inner diameter) 25.4 mm long cannula with a force not exceeding 25 N.

16. A method of treating a subject with an injectable aqueous implant formulation, wherein the subject is in need of oral tissue regeneration, comprising implanting the injectable aqueous implant formulation of claim 1 in an oral cavity of the subject by extruding the injectable aqueous implant formulation of claim 1 through a tapering system and a gauge 18 (having an inner diameter of 0.838 mm) 25.4 mm long cannula positioned in the implantation site.

17. The method of claim 16, wherein the subject is in need of regeneration of alveolar bone, root cementum or periodontal ligament and said implanting promotes regeneration of alveolar bone, root cementum or periodontal ligament in the subject's oral cavity.

18. The method of claim 16, wherein the injectable aqueous implant formulation has been stored in a syringe for up to 9 months.

19. The method of claim 16, wherein the injectable aqueous implant formulation is extruded through a tapering system and an 18 gauge (0.838 mm inner diameter) 25.4 mm long cannula with a force not exceeding 25 N.

\* \* \* \* \*